(12) United States Patent
Ganesan et al.

(10) Patent No.: US 7,763,760 B2
(45) Date of Patent: *Jul. 27, 2010

(54) CATALYST COMPOSITION AND METHOD FOR HALOGENATING AROMATIC COMPOUNDS

(75) Inventors: Balakrishnan Ganesan, Maharashtra (IN); Pradeep Jeevaji Nadkarni, Karnataka (IN)

(73) Assignee: SABIC Innovative Plastics IP B.V. (NL)

( * ) Notice: Subject to any disclaimer, the term of this patent is extended or adjusted under 35 U.S.C. 154(b) by 1406 days.

This patent is subject to a terminal disclaimer.

(21) Appl. No.: 10/870,353

(22) Filed: Jun. 16, 2004

(65) Prior Publication Data

US 2005/0283035 A1    Dec. 22, 2005

(51) Int. Cl.
*C07C 17/00*    (2006.01)
(52) U.S. Cl. .............. 570/207; 570/182; 570/201; 570/208
(58) Field of Classification Search .......... 570/207, 570/182, 201, 208
See application file for complete search history.

(56) References Cited

U.S. PATENT DOCUMENTS

| | | |
|---|---|---|
| 3,226,447 A | 12/1965 | Bing et al. |
| 4,031,142 A | 6/1977 | Graham |
| 4,031,145 A | 6/1977 | Di Bella |
| 4,031,147 A | 6/1977 | Graham |
| 4,190,609 A | 2/1980 | Lin |
| 4,250,122 A | 2/1981 | Lin et al. |
| 4,289,916 A | 9/1981 | Nakayama et al. |
| 4,647,709 A | 3/1987 | Wolfram |
| 4,925,994 A | 5/1990 | Mais et al. |
| 5,053,565 A | 10/1991 | Botta et al. |
| 5,210,343 A | 5/1993 | Mais et al. |
| 7,012,166 B2 * | 3/2006 | Hancu et al. ............. 570/201 |

FOREIGN PATENT DOCUMENTS

| | | |
|---|---|---|
| EP | 0 126 669 | 11/1984 |
| NL | 7505531 A | 11/1976 |

OTHER PUBLICATIONS

International Search Report dated Jul. 27, 2006.
Peng Cheng et al., "Crystal Structure and Ferromagnetic Behavior of a µ-acetato-bridged One-Dimensional Linear-Chain Copper (II) Complex", Inorganica Chimica Acta, vol. 254, No. 2, pp. 371-373, 1997.
M. J. Baillie et al., "Copper (II) Salts of Very Strong Acids", Chemical Communications, pp. 91-92, 1965.
M. A. Khan et al., "Theoretical Aspects of An Equilibrium Study in the Non-Dissociating Molecular Solvent Acetic Acid", Polyhedron, vol. 9, No. 21, pp. 2613-2617, 1990.
M. A. Khan et al., "Stability, Spectra and Structure of the Copper (II) Chloride Complexes in Acetic Acid", Polyhedron, vol. 2, No. 6, pp. 459-463, 1982.
D. C. Nonhebel, "Acylation of Metal Chelates. Part II. The Anomalous Behaviour of Copper (II) Chelates", Journal of the Chemical Society, pp. 4628-4632, May 2, 1962.
Hassan Ali Dessouki et al., "Physicochemical Studies on Metal Complexes of Some o-Hydroxy and o-Carboxyphenylazo-β-Diketones", Acta Chimica Hungarica, vol. 126, No. 5, pp. 653-663, 1989.
Y. Y. Lim et al., "Autooxidation of Catechols in Solutions of Copper (II) Surfactants and Hydrated Metal Ions in Sodium Dodecyl Sulphate", Journal of Molecular Catalysis, vol. 85, pp. 173-181, 1993.

* cited by examiner

*Primary Examiner*—Jafar Parsa
*Assistant Examiner*—Sudhakar Katakam

(57) ABSTRACT

A method for ring-halogenating an aromatic compound comprises contacting with chlorine or bromine, a mixture comprising the aromatic compound and a mixed copper salt of formula Cu(Y)X, where Y comprises a counterion derived from an organic acid, where the organic acid has a pKa relative to water of 0 or greater; and X comprises Cl, Br, I, or $(SO_4^{2-})_{1/2}$; to produce a reaction mixture comprising a haloaromatic compound and a copper(II) halide residue.

32 Claims, No Drawings

US 7,763,760 B2

CATALYST COMPOSITION AND METHOD FOR HALOGENATING AROMATIC COMPOUNDS

BACKGROUND

This invention relates to the halogenation of aromatic compounds. More particularly, it relates to chlorination methods and catalyst compositions capable of producing predominantly para-chloro aromatic compounds.

Chlorination of aromatic compounds such as toluene and xylenes is a known reaction affording useful compounds. The most useful of these compounds for many purposes are the para-chloro aromatic compounds. para-Chlorotoluene, for example, is an intermediate capable of conversion into many useful chemicals. para-Chloro-ortho-xylene (also sometimes referred to as 4-chloro-1,2-dimethylbenzene) is another useful compound, which can be oxidized to 4-chlorophthalic acid, which is in turn an important intermediate in the production of polyetherimides. However, the production of these useful para-chloroaromatic compounds is complicated by the simultaneous production of numerous undesirable by-products. Thus, chlorination of toluene and xylenes, such as ortho-xylene produces the para-monochloro isomer in admixture with other isomers, such as ortho-chlorotoluene and 3-chloro-1,2-dimethylbenzene, respectively. In addition, numerous polychlorinated products are also generally produced.

Many of the known methods for chlorination of aromatic compounds involve reaction with elemental chlorine in the presence of Lewis acids, such as for example, ferric chloride, antimony trichloride, antimony pentachloride, zinc chloride and aluminum chloride, which are also generally used as catalysts in Friedel-Crafts reactions, such as alkylation and acylation.

However, the use of such catalysts generally does not lead to enhanced selectivity for the desired para-chloroaromatic isomer and minimized formation of polychlorinated products. Various publications, including many U.S. patents, go further in describing mixed catalyst systems in which another catalyst component is an organosulfur compound. The organosulfur compounds disclosed in these publications are of very diverse structures. Some examples of organosulfur compounds that have been used include phenoxathiins, thianthrenes, and phenothiazines. Illustrative patents are U.S. Pat. Nos. 3,226,447, 4,031,142, 4,031,145, 4,031,147, 4,190,609, 4,250,122, 4,289,916, 4,647,709, 4,925,994, and 5,210,343; and European Patent Application No. 126669. Progress in the field of para halogenation of aromatic compounds notwithstanding, there remains a strong need to develop further improvements both in terms of product yield and selectivity.

BRIEF SUMMARY

The present invention provides methods and catalyst compositions for formation primarily of a para-chloroaromatic compound. The methods can be easily translated into a commercial operation.

In one embodiment of the present invention, a method for ring-halogenating an aromatic compound comprises contacting with chlorine or bromine, a mixture comprising the aromatic compound and a mixed copper salt of formula Cu(Y)X, where Y comprises a counterion derived from an organic acid, where the organic acid has a pKa relative to water of 0 or greater; and X comprises Cl, Br, I, or $(SO_4^{2-})_{1/2}$; to produce a reaction mixture comprising a haloaromatic compound and a copper(II) halide residue.

In a second embodiment of the invention, a method for ring-chlorinating toluene or ortho-xylene comprises contacting with chlorine, a mixture comprising toluene or ortho-xylene, and a mixed copper salt of formula Cu(Y)X, wherein Y comprises a counterion derived from an organic acid, said organic acid having a pKa relative to water of 0 or greater; and X comprises Cl, Br, I, or $(SO_4^{2-})_{1/2}$.

In a third embodiment of the invention, a method for ring-chlorinating toluene or ortho-xylene comprises contacting toluene or ortho-xylene with chlorine in the presence of a catalyst composition, where the catalyst composition comprises at least one mixed copper salt having a formula: Cu(Y)X, wherein Y comprises a counterion derived from an organic acid, said organic acid having a pKa relative to water of 0 or greater; and X comprises Cl, Br, I, or $(SO_4^{2-})_{1/2}$; and at least one organic sulfur compound selected from the group consisting of phenothiazine-N-carbonyl chloride, N-trifluoroacetylphenothiazine, 3-chloro-N-trifluoroacetylphenothiazine, and 3-trifluoromethyl-N-trifluoroacetylphenothiazine.

A fourth embodiment of the invention is a mixed copper salt having a formula: Cu(Y)X, wherein Y comprises a counterion derived from an organic acid, said organic acid having a pKa relative to water of 0 or greater; and X comprises Cl, Br, I, or $(SO_4^{2-})_{1/2}$.

In a fifth embodiment of the invention, a method for forming a mixed copper salt comprises the step of contacting an inorganic copper(II) salt $CuX_2$, wherein X is independently Cl, Br, I, or $(SO_4^{2-})_{1/2}$; with a salt of an organic acid; wherein said organic acid has a pKa relative to water of 0 or greater; and the mixed copper salt has the formula: Cu(Y)X, wherein Y comprises a counterion derived from the organic acid; and X comprises Cl, Br, I, or $(SO_4^{2-})_{1/2}$.

In a sixth embodiment of the invention, a catalyst composition for ring-chlorinating an aromatic compound comprises the reaction product of at least one organic sulfur compound, a chlorine atom source, and a mixed copper salt having a formula: Cu(Y)X, wherein Y comprises a counterion derived from an organic acid, said organic acid having a pKa relative to water of 0 or greater; and X comprises Cl, Br, I, or $(SO_4^{2-})_{1/2}$. to water of 0 or greater; and X comprises chloride, bromide, iodide, or sulfate.

In a seventh embodiment of the invention, a method for chlorinating an aromatic compound comprises contacting the aromatic compound with chlorine in the presence of a catalyst composition prepared by combining in the presence of a chlorine atom source, a mixture comprising at least one organic sulfur compound, and a mixed copper salt of formula: Cu(Y)X, wherein Y comprises a counterion derived from an organic acid, said organic acid having a pKa of 0 or greater; and X comprises Cl, Br, I, or $(SO_4^{2-})_{1/2}$.

In an eighth embodiment of the invention, a method for chlorinating an aromatic compound comprises contacting the aromatic compound with chlorine in the presence of a catalyst composition prepared by (1) combining a chlorine atom source with a mixed copper salt of formula: Cu(Y)X, wherein Y comprises a counterion derived from an organic acid, said organic acid having a pKa of 0 or greater; and X comprises Cl, Br, I, or $(SO_4^{2-})_{1/2}$ to form an activated copper(II) chloride; and (2) combining the activated copper(II) chloride with at least one organic sulfur compound to form said catalyst composition.

DETAILED DESCRIPTION

The embodiments described above have many advantages, such as providing catalyst compositions, and methods for using these catalyst compositions to promote efficient para-selective ring-halogenations of aromatic compounds, such as toluene and ortho-xylene.

Any aromatic compound may be chlorinated by the methods disclosed herein. Suitable aromatic compounds include monocyclic and polycyclic hydrocarbons, and substituted derivatives thereof. Non-limiting examples of monocyclic hydrocarbons include benzene, toluene, ortho-, meta-, and para-xylene; and 1,2,4,5-tetramethylbenzene. It is preferred that the aromatic hydrocarbon contains at least one $C_{1-4}$ alkyl substituent, preferably methyl, and that a para-position with respect to one of the alkyl groups be substituted with hydrogen. Most preferred are toluene and ortho-xylene.

In an embodiment of the invention, the aromatic compound is contacted with chlorine in the presence of a catalyst composition to effect reaction. For liquid aromatic compounds, chlorine gas is generally bubbled through the liquid reactant. A solvent may be used with liquid aromatic compounds, although solvent is ordinarily not necessary. For aromatic compounds that are solids at ambient temperatures, a solvent can be beneficially used. Typically, the reaction takes place preferably in the liquid phase rather than in the vapor phase.

For the sake of brevity, the constituents of the catalyst composition are defined as "components" irrespective of whether a reaction involving said constituents occurs before or during the chlorination reaction. Thus, the catalyst composition may include the reaction products derived from one or more of the components. Such reaction products may comprise a chlorine atom source, such as chlorine, hydrogen chloride, or various combinations of chlorine and hydrogen chloride. Further, such reaction products may or may not be in admixture with one or more unreacted components remaining in the catalyst combination. Generally, the catalyst composition is obtained by combining components (A), (B), and (C).

Component (A) of the catalyst composition is a mixed copper salt of formula: Cu(Y)X, where Y comprises a counterion derived from an organic acid, which has a pKa of 0 or greater; and X comprises Cl, Br, I, or $(SO_4^{2-})_{1/2}$. Although it is not necessary for the metal salt to be soluble in the reaction medium, preferred mixed copper salts include those that are at least partially soluble in the reaction medium. Included in this sub-category are salts where the Y anion (also hereinafter sometimes called the counterion) is derived from an acidic organic compound. Such salts have at least some solubility in a hydrophobic, organic solvent, such as for example, toluene and ortho-xylene. Illustrative examples of such acidic organic compounds include, but are not limited to, those with an approximate pKa value relative to water in a first embodiment of zero to about 1, in a second embodiment of at least about 1, in a third embodiment of at least about 2, in a fourth embodiment of at least about 3, in a fifth embodiment of at least about 4, in a sixth embodiment of at least about 5, in a seventh embodiment of at least about 6, and in an eighth embodiment of at least about 7, and in a ninth embodiment of at least about 8, and in a tenth embodiment of at least 9. In some embodiments, the anion is derived from a carboxylic acid, such as for example, a monocarboxylic acid or a derivative thereof, or a 2,4-dione or a derivative thereof. By "2,4-dione" is meant a 1,3-dicarbonyl compound including, but not limited to, a diketone or a beta-ketoester in which a carbon atom having at least one acidic hydrogen separates the two carbonyl groups, irrespective of the placement of the carbonyl groups in the molecule. Illustrative examples of derivatives of carboxylic acids or 2,4-diones include halogenated derivatives and particularly chlorinated or fluorinated derivatives. Other non-limiting examples of counterions derived from organic acids include phosphate, phosphonate, alkoxide, phenoxide, and the like. Specific examples of salts suitable as component (A) include, but are not limited to cupric(benzoate)chloride, cupric(benzoate)bromide, cupric(benzoate)sulfate; cupric (acetate)chloride, cupric(acetate)bromide, cupric(acetate) sulfate, cupric(trifluoroacetate)chloride, cupric(trifluoroacetate)bromide, cupric(trifluoroacetate)iodide, cupric (trifluoroacetate)sulfate, cupric(stearate)chloride, cupric (stearate)bromide, and cupric(stearate)sulfate, cupric (pentafluorophenylbenzoate)chloride, cupric (pentafluorophenylbenzoate)bromide, cupric (pentafluorophenyl)sulfate, and mixtures of the foregoing mixed copper salts. Copper(benzoate)chloride is preferred since it is inexpensive and can be readily prepared using methods which are described below. Combinations of various salts can also be used.

Component (B) is at least one organic sulfur compound. Suitable compounds include dialkyl and diaryl sulfides, dialkyl and diaryl disulfides, alkyl and aryl mercaptans, phenoxathiin, thiophene, dibenzothiophene, thianthrene and phenothiazine, including substituted derivatives thereof. Component B may also be a mixture of organic sulfur compounds.

A particularly preferred organic sulfur compound is phenothiazine-N-carbonyl chloride, having the formula

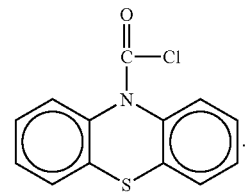

It may be synthesized by known methods such as the reaction of phenothiazine with phosgene. Also particularly effective is N-trifluoroacetylphenothiazine. Substituted analogs of N-trifluoroacetylphenothiazine, for example where the substituent is located on the aromatic ring, such as for example, 2-chloro-N-trifluoroacetylphenothiazine and 2-trifluoromethyl-N-trifluoroacetylphenothiazine are also effective.

Component (C) is a source of halogen atoms such as a dihalogen, or a hydrogen halide, such as hydrogen chloride. In some circumstances, organic sulfur compounds, such as phenothiazine-N-carbonyl chloride can also act as a source of halide atoms, in addition to their role as a cocatalyst (Component B). In an embodiment, the hydrogen halide can be a commercially available material, such as for example hydrogen chloride gas from a cylinder. In another embodiment, the hydrogen halide is generated in-situ from the electrophilic aromatic substitution reaction of an aromatic compound with a source of electrophilc halogen. Without wishing to be bound by any theory, Applicants believe that component (C) reacts rapidly with the metal salt to generate a metal halide in a finely divided state, which in combination with the organic sulfur compound leads to selective halogenation of the aromatic compound.

The reaction of externally provided Component (C) with a metal salt is a valuable method for producing suspensions of finely divided metal halides, which can be used as catalysts having high activity, not only for aromatic halogenations, but also for any reaction which requires a Lewis acid catalyst, such as for example, the Friedel Crafts reaction and other related reactions. The process of generating the metal halide can be conducted in any organic solvent that is chemically inert to the hydrogen halide. Suitable organic solvents include saturated hydrocarbon solvents, such as for example, pentane, hexane, heptane, octane, decane, tetralin, and the like; aromatic hydrocarbons, such as for example, toluene, xylene, mesitylene, and the like.

The method of chlorinating aromatic compounds, as disclosed herein, takes advantage of the fact that either the chlorine directly, or the hydrogen halide generated in-situ from electrophilic aromatic substitution reaction of a source of electrophilic halogen with an aromatic compound reacts rapidly with the metal salt to generate the finely divided metal halide, which together with the organic sulfur compound leads to formation of selectively halogenated aromatic compounds. The method of the invention may be performed by contacting a mixture of the aromatic compound, component (A), and component (B) with chlorine, preferably in the liquid phase, most often at a temperature in the range of about 0-100° C., preferably about 5-50° C., and most preferably below 25° C. Preferably, the reaction mixture is protected from air and moisture by contact with an inert gas such as nitrogen or argon, and is shielded from exposure to ambient light to minimize chlorination of alkyl side chains on the aromatic compound. The term "light" in this context means radiation in the visible and ultraviolet regions of the spectrum. It is also important to shield the reaction mixture from moisture. The level of moisture in the aromatic compound to be halogenated should be preferably less than or equal to about 50 parts per million in one embodiment, more preferably less than or equal to about 25 parts per million in another embodiment.

On a preparative scale, contact is preferably accomplished by passing at least a portion, and more preferably substantially all of the chlorine through the reaction mixture. However, for screening purposes, it is often convenient to charge the chlorine to the head space of the reaction system, and to remove by-product hydrogen chloride by applying a slight vacuum. The pressure at which the reaction is carried out may vary from sub-atmospheric to super-atmospheric, for example from about 0.5-10 atmospheres, although super-atmospheric pressure is generally not necessary. It is also within the scope of the invention to generate chlorine in situ from a reagent such as thionyl chloride, sulfuryl chloride, phosgene, oxalyl chloride, N-chlorosuccinimide, and the like. On a preparative scale, chlorine gas can simply be passed into the mixture with periodic sampling until the desired or maximum amount of the desired para-monochloroaromatic compound product has been produced, as determined by analytical methods known in the art; for example, gas chromatography. For screening purposes it has been found convenient to employ an excess of chlorine, typically up to about 50 mole %, and preferably about 10-30 mole % relative to the aromatic compound. On a preparative scale, however, the use of excess chlorine is generally to be avoided since it leads to over-chlorination. In preparative runs, typically, 25-100 mole percent, preferably 50-90 mole percent, and most preferably 70-85 mole percent of chlorine is employed relative to the amount of aromatic compound being chlorinated. In the preparative reactions, the efficiency for use of the chlorine is nearly 100 percent, so excess chlorine inevitably leads to over-chlorination.

The proportion of component (A) is typically in a of range from about 0.005 to about 10.0%, and the proportion of component (B) is in a range of from about 0.005 to about 10.0% by weight based on the weight of the aromatic compound. Preferably, the proportions of components (A) and (B) are, respectively, about 0.01-5.0% and about 0.01-0.1%, and most preferably about 0.07-3.0% and about 0.05-0.1%. The weight ratio of component (A) to component (B) is in various embodiments in a range of between about 2000:1 and 1:2000. The weight ratio of component (A) to component (B) is in some particular embodiments in a range of between about 2:1 and about 100:1; in other embodiments in a range of between about 3:1 and about 80:1; and in still other embodiments in a range of between about 3:1 and about 70:1.

In an alternative method for chlorinating an aromatic compound, a two step process can be used in which the first step is the reaction of a mixed copper salt of formula Cu(Y)X with hydrogen chloride gas in an aromatic hydrocarbon solvent, which also serves as the substrate for a subsequent aromatic ring chlorination reaction. After forming the finely divided copper chloride catalyst, an organic sulfur compound can be added to the copper chloride to form a catalyst composition, followed by passage of chlorine gas to form the ring-chlorinated product in high selectivity.

While the present invention is not dependent in any way on theory or reaction mechanism, it is believed that these differences in proportion of metal compound are the result of different reaction mechanisms. With a relatively strong Lewis acid such as ferric chloride as Component (A), it is believed that complex formation with component (B) minimizes the level of non-selective aromatic ring chlorination catalyzed by the Lewis acid alone, and promotes selective chlorination with production of the para-monochlorinated isomer. The copper-based Lewis acids employed according to the present invention, by contrast, are relatively weak and their presence in relatively large proportions is not as likely to afford non-selective aromatic chlorination, although selectivity is improved by the presence of component (B). When aromatic compounds having alkyl substituents are used, at low Lewis acid levels, side chain chlorination predominates to yield products that are undesirable for the purposes of the present invention. Applicants have found that a copper(II) chloride catalyst, generated as a finely divided suspension in the reaction mixture by the action of hydrogen chloride on a mixed copper salt of formula Cu(Y)X (where Y and X are as described previously) a surprisingly higher catalytic activity and high selectivity, as compared with chemically identical, but commercially available samples of copper(II) chloride. Furthermore, the in-situ generated metal halide in combination with an organic sulfur compound shows a surprisingly higher catalytic activity and selectivity for forming the para-chloroaromatic compound. Empirical observations indicate that a metal salt that is relatively more soluble in the hydrophobic solvent leads to a metal chloride having a relatively smaller particle size. Metal salts having fluorine-containing 2,4-pentanedione groups are generally more soluble in a hydrophobic solvent, and hence would be expected to generate relatively smaller particles of the metal halide. Under the reaction conditions employed for halogenation of aromatic compounds, the reaction of hydrogen halide with a metal salt can proceed to generate one or more metal halide catalyst species. For example, if zirconium tetrakis(acetylacetonate) is used as the metal salt, various metal halide catalyst species corresponding to the formula, $Zr(AcAc)_m X_{4-m}$, where "m" has a value of 1 to 3, and X is chlorine or bromine, are generated initially. However, as the chlorination of the aromatic compound continues, these initially formed catalyst species eventually transform into highly active, finely divided zirconium(IV) chloride, which together with the organic sulfur compound promotes the selective para-halogenation of the aromatic compound. Similarly, when copper(II) benzoate or copper(benzoate) chloride is used as the metal salt (Component A), reaction with hydrogen chloride generates finely divided particles of copper(II) chloride, which can be verified by analytical techniques, such as powder X-ray diffraction analysis (XRD).

The mixed copper salts are prepared by contacting inorganic copper(II) salts, such as copper(II)chloride, copper(II) bromide, copper(II) iodide, copper(II)sulfate, or mixtures thereof, with an stoichiometric quantity of a salt of an organic acid, preferably an alkali metal salt of an organic acid having a pKa relative to water of 0 or greater. Preferred metal salts are lithium, sodium, potassium, rubidium, or cesium salts of monocarboxylic acids. Any solvent in which the copper(II) halide is soluble can be used. Preferred solvents are those in which the starting copper(II) halide is soluble, but in which solvent the Cu(Y)X salts are insoluble, to allow for easy isolation of the product. Preferred solvents are those comprising water or $C_1$-$C_4$ aliphatic alcohols.

In situations where conditions are optimized for production of the desired para-chloroaromatic compound, it may be possible to employ the chlorination product of the method of the invention directly for further purposes, for example as a chemical intermediate, without further purification. Sometimes, however, further purification is desirable or necessary. Purification may be achieved by the use of one or more conventional purification techniques, including fractional distillation, fractional crystallization, and preparative-scale chromatographic methods. [0032] The catalyst compositions taught herein may be employed for any reaction catalyzed by (1) the combination of (A) at least one mixed copper salt of formula Cu(Y)X, and (B) at least one organic sulfur compound; (2) a reaction product comprising (A) and (B), (3) the components (A), (B), and a reaction product comprising at least one of (A) or (B), or (4) (B) and a reaction product of component (A) with a hydrogen halide (as described previously). Illustrative applications of the catalyst compositions include, but are not limited to, halogenation reactions (e.g. chlorination, bromination, iodination), and Friedel-Crafts reactions.

The catalyst compositions and methods disclosed herein are especially useful for producing 4-chloro-ortho-xylene by the chlorination of ortho-xylene, and allow high ortho-xylene conversion while keeping the selectivity for mono-chloro-ortho-xylene at relatively high levels, and formation of over-chlorinated products at relatively lower levels. This increases the efficiency of recovering purified 4-chloro-ortho-xylene by downstream operations, such as distillation, and also decreases the cost of recovery and recycle of unreacted ortho-xylene by distillation.

EXAMPLES

The invention is illustrated by the following examples. All percentages are by weight. Example numbers with an asterisk ("*") after the number indicate comparative examples. The abbreviation "PNCC" stands for N-chlorocarbonyl phenothiazine. "Conversion" is the percentage of ortho-xylene converted to chlorinated products. The abbreviation "mono-Cl", which designates the amount of ring mono-chlorinated ortho-xylene products, and does not include products in which the side chain is chlorinated, is given as a percentage of total chlorinated products. The abbreviation "4-Cl" designates the amount of the 4-monochloro (p-chloro) isomer as a percentage of total aromatically monochlorinated products.

Example 1

This experiment describes the preparative scale chlorination of ortho-xylene using cupric(benzoate) chloride as Component (A) and PNCC as the organic sulfur compound (Component B).

In a 2-liter, four necked round bottom flask fitted with an overhead stirrer, a gas bubbler for chlorine gas, a gas outlet connected to water and alkali scrubbers, and a thermometer, was placed ortho-xylene (1100 grams), PNCC (0.22 gram), and cupric(benzoate) chloride (8.8 grams, pre-dried at 50° C. for 48 hours). The reaction flask was covered to avoid exposure of the reaction mixture to ambient light during the chlorination reaction. The contents of the flask were cooled while stirring to about 5° C., and chlorine gas was introduced at the rate of 1.5-2 moles per hour. The reaction was exothermic, and the reaction temperature was maintained at a between about 5-8° C. by externally cooling the reaction mixture, as well as by controlling the flow of chlorine. Within the first two minutes of passing chlorine gas, a brown precipitate was formed, which was sampled and confirmed by powder X-ray diffraction analysis to be copper(II) chloride. The passage of chlorine gas was continued, and the reaction was monitored for ortho-xylene conversion by gas chromatography. When an ortho-xylene conversion of 70-75% was reached, the chlorine flow into the reaction mixture was stopped, and thereafter nitrogen was bubbled through the reaction mixture for about 30 minutes to remove unreacted chlorine gas as well as dissolved hydrogen chloride gas.

The same procedure was repeated with a commercial sample of copper(II) chloride (Comparative Example 1). The results are shown in Table 1.

TABLE 1

| Example | Lewis acid | | Conversion, % | Mono-Cl, % | 4-Cl, % |
|---|---|---|---|---|---|
| | Identity | wt % | | | |
| 1 | CuCl(OCOC$_6$H$_5$) | 0.8 | 78 | 97 | 80 |
| 1* | CuCl$_2$ | 0.8 | 63 | 44 | 58 |

Table 1 clearly shows that cupric(benzoate)chloride functions more effectively, as seen from the higher conversion and 4-chloro-ortho-xylene selectivity, as compared to commercially available copper(II) chloride.

Example 2

This Example describes the preparation of copper(benzoate) chloride.

Equimolar quantities of copper(II) chloride and sodium benzoate were separately weighed out and dissolved in water. The sodium benzoate solution was added to the solution of copper(II) chloride with stirring. The resulting precipitate of copper(benzoate) chloride was filtered, washed with water until the washings did not contain any sodium benzoate or copper(II) chloride, then washed with acetone to remove any traces of copper(II) benzoate, and finally dried at about 50° C. and about 10 millibar vacuum for at least 48 hours to furnish the desired product as a pale blue powder. The product can be stored under ambient atmosphere. The infrared spectrum of the product showed the following absorptions (in cm$^{-1}$): 1595 (s), 1550 (s), 1420 (s), 923 (m), 873 (m), 704 (m). The notations "s", and "m" stand for stand for "strong" and "medium", and represent the intensity of the absorptions.

The procedure described in Example 2 can be carried out using copper(II) sulfate instead of copper(II) chloride as the starting material to provide copper(benzoate) (sulfate)$_{1/2}$ as a pale blue powder.

While typical embodiments have been set forth for the purpose of illustration, the foregoing descriptions and examples should not be deemed to be a limitation on the scope of the invention. Accordingly, various modifications, adaptations, and alternatives may occur to one skilled in the art without departing from the spirit and scope of the present invention.

The invention claimed is:

1. A method for ring-halogenating an aromatic compound, which comprises contacting with chlorine or bromine, a mixture comprising the aromatic compound and a mixed copper salt of formula Cu(Y)X, wherein Y comprises a counterion derived from an organic acid, said organic acid having a pKa relative to water of 0 or greater; and X comprises Cl, Br, I, or $(SO_4^{2-})_{1/2}$; to produce a reaction mixture comprising a haloaromatic compound and a copper(II) halide residue.

2. The method of claim 1, wherein said mixture further comprises at least one organic sulfur compound.

3. The method of claim 2, wherein said at least one organic sulfur compound comprises a dialkyl sulfide, a diaryl sulfide, an alkyl mercaptan, an aryl mercaptan, a phenoxathiin, a thiophene, a dibenzothiophene, a thianthrene, a phenothiazine, or mixtures of the foregoing organic sulfur compounds.

4. The method of claim 2, wherein said at least one organic sulfur compound is selected from the group consisting of phenothiazine-N-carbonyl chloride, N-trifluoroacetylphenothiazine, 3-chloro-N-trifluoroacetylphenothiazine, 3-trifluoromethyl-N-trifluoroacetylphenothiazine, and mixtures of the foregoing organic sulfur compounds.

5. The method of claim 1, wherein said organic acid is selected from the group consisting of a monocarboxylic acid or a derivative, and a 2,4-dione or a derivative.

6. The method of claim 1, wherein Y comprises acetate, benzoate, 1,1,1-trifluoro-2,4-pentanedionate, 1,1,1,5,5,5-hexafluoro-2,4-pentanedionate, or 2,4-pentanedionate; and X comprises Cl, Br, I, or $SO_4$.

7. The method of claim 1, wherein said mixed copper salt is selected from the group consisting of cupric(benzoate) chloride, cupric(benzoate)bromide, cupric(benzoate)sulfate; cupric(acetate)chloride, cupric(acetate)bromide, cupric(acetate)sulfate, cupric(trifluoroacetate)chloride, cupric(trifluoroacetate)bromide, cupric(trifluoroacetate)iodide, cupric(trifluoroacetate)sulfate, cupric(stearate)chloride, cupric(stearate)bromide, and cupric(stearate)sulfate, cupric(pentafluorophenylbenzoate)chloride, cupric(pentafluorophenylbenzoate)bromide, cupric(pentafluorophenyl)sulfate, and mixtures of the foregoing mixed copper salts.

8. The method of claim 1, wherein said contacting takes place in the liquid phase.

9. The method of claim 1, wherein said contacting comprises a reaction temperature of about 0-100° C.

10. The method of claim 1, wherein said contacting comprises shielding from exposure to ambient light and ambient moisture.

11. The method of claim 1, wherein the aromatic compound is a monocyclic hydrocarbon.

12. The method of claim 1, wherein the aromatic compound is toluene or ortho-xylene.

13. The method of claim 1, wherein said mixed copper salt is present in an amount from about 0.005-10.0% by weight based on the aromatic compound.

14. The method of claim 1, wherein said mixed copper salt is present in an amount from about 0.07-3.0% by weight based on the aromatic compound.

15. The method of claim 2, wherein the proportion of said at least one organic sulfur compound is present in an amount from about 0.005-10.0% by weight based on the aromatic compound.

16. The method of claim 2, wherein said at least one organic sulfur compound is present in an amount from about 0.01-0.1% by weight based on the aromatic compound.

17. A method for ring-chlorinating toluene or ortho-xylene, which comprises contacting with chlorine, a mixture comprising toluene or ortho-xylene, and a mixed copper salt of formula Cu(Y)X, wherein Y comprises a counterion derived from an organic acid, said organic acid having a pKa relative to water of 0 or greater; and X comprises Cl, Br, I, or $(SO_4^{2-})_{1/2}$.

18. The method of claim 17, wherein said mixture further comprises at least one organic sulfur compound.

19. The method of claim 18, wherein said at least one organic sulfur compound comprises a dialkyl or diaryl sulfide, an alkyl or aryl mercaptan, a phenoxathiin, a thiophene, a dibenzothiophene, a thianthrene, a phenothiazine, or mixtures of the foregoing organic sulfur compounds.

20. The method of claim 18, wherein said at least one organic sulfur compound is selected from the group consisting of phenothiazine-N-carbonyl chloride, N-trifluoroacetylphenothiazine, 3-chloro-N-trifluoroacetylphenothiazine, 3-trifluoromethyl-N-trifluoroacetylphenothiazine, and mixtures of the foregoing organic sulfur compounds.

21. The method of claim 17, wherein Y comprises acetate, benzoate, 1,1,1-trifluoro-2,4-pentanedionate, 1,1,1,5,5,5-hexafluoro-2,4-pentanedionate, 2,4-pentanedionate, or oxalate; and X comprises Cl or Br.

22. A method for ring-chlorinating toluene or ortho-xylene, which comprises contacting toluene or ortho-xylene with chlorine in the presence of a catalyst composition, wherein said catalyst composition comprises:
  at least one mixed copper salt having a formula: Cu(Y)X, wherein Y comprises a counterion derived from an organic acid, said organic acid having a pKa relative to water of 0 or greater; and X comprises Cl, Br, I, or $(SO_4^{2-})_{1/2}$; and
  at least one organic sulfur compound selected from the group consisting of phenothiazine-N-carbonyl chloride, N-trifluoroacetylphenothiazine, 3-chloro-N-trifluoroacetylphenothiazine, and 3-trifluoromethyl-N-trifluoroacetylphenothiazine.

23. The method of claim 22, wherein said at least one mixed copper salt is selected from the group consisting of cupric (benzoate)chloride, cupric (benzoate)bromide, cupric (benzoate)sulfate; cupric(acetate)chloride, cupric(acetate) bromide, cupric(acetate)sulfate, cupric(trifluoroacetate) chloride, cupric(trifluoroacetate)bromide, cupric (trifluoroacetate)iodide, cupric(trifluoroacetate)sulfate, cupric(stearate)chloride, cupric(stearate)bromide, and cupric (stearate)sulfate, cupric(pentafluorophenylbenzoate)chloride, cupric(pentafluorophenylbenzoate)bromide, cupric (pentafluorophenyl)sulfate, and mixtures of the foregoing mixed copper salts.

24. The method of claim 22, wherein the catalyst composition comprises at least one reaction product of said at least one mixed copper salt, said at least one organic sulfur compound, and a chlorine atom source.

25. The method of claim 24, wherein said chlorine atom source comprises molecular chlorine or hydrogen chloride.

26. A method for chlorinating an aromatic compound, which comprises contacting the aromatic compound with chlorine in the presence of a catalyst composition prepared by combining in the presence of a chlorine atom source, a mixture comprising at least one organic sulfur compound, and a mixed copper salt of formula: Cu(Y)X, wherein Y comprises a counterion derived from an organic acid, said organic acid having a pKa of 0 or greater; and X comprises Cl, Br, I, or $(SO_4^{2-})_{1/2}$.

27. The method of claim 26, wherein said at least one organic sulfur compound is selected from the group consisting of phenothiazine-N-carbonyl chloride, N-trifluoroacetylphenothiazine, 3-chloro-N-trifluoroacetylphenothiazine and 3-trifluoromethyl-N-trifluoroacetylphenothiazine.

28. The method of claim 26, wherein said catalyst composition comprises at least one reaction product of said mixed copper salt, said at least one organic sulfur compound, and said chlorine atom source.

29. The method of claim 26, wherein said chlorine atom source is selected from the group consisting of molecular chlorine, hydrogen chloride, and phenothiazine-N-carbonyl chloride.

30. The method of claim 29, wherein said hydrogen chloride is generated from reaction of molecular chlorine with said aromatic compound.

31. The method of claim 26, wherein said at least one organic sulfur compound comprises a dialkyl sulfide, a diaryl sulfide, an alkyl mercaptan, an aryl mercaptan, a phenoxathiin, a thiophene, a dibenzothiophene, a thianthrene, a phenothiazine, or mixtures of the foregoing organic sulfur compounds.

32. A method for chlorinating an aromatic compound, which comprises contacting the aromatic compound with chlorine in the presence of a catalyst composition prepared by (1) combining a chlorine atom source with a mixed copper salt of formula: Cu(Y)X, wherein Y comprises a counterion derived from an organic acid, said organic acid having a pKa of 0 or greater; and X comprises Cl, Br, I, or $(SO_4^{2-})_{1/2}$ to form an activated copper(II) chloride; and (2) combining said activated copper(II) chloride with at least one organic sulfur compound to form said catalyst composition.

* * * * *